US007778693B2

(12) United States Patent
Barbour et al.

(10) Patent No.: US 7,778,693 B2
(45) Date of Patent: Aug. 17, 2010

(54) SYSTEM AND METHOD FOR QUANTIFYING THE DYNAMIC RESPONSE OF A TARGET SYSTEM

(75) Inventors: Randall L. Barbour, Glen Head, NY (US); Yaling Pei, Morris Plains, NJ (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 581 days.

(21) Appl. No.: 10/408,510

(22) Filed: Apr. 7, 2003

(65) Prior Publication Data

US 2004/0039268 A1    Feb. 26, 2004

Related U.S. Application Data

(60) Provisional application No. 60/370,305, filed on Apr. 6, 2002.

(51) Int. Cl.
*A61B 6/00* (2006.01)
(52) U.S. Cl. .................... 600/473; 600/475; 600/328
(58) Field of Classification Search ................ 600/328, 600/473, 475
See application file for complete search history.

(56) References Cited

U.S. PATENT DOCUMENTS

| 5,137,355 | A | | 8/1992 | Barbour et al. | |
|---|---|---|---|---|---|
| 5,467,767 | A | * | 11/1995 | Alfano et al. | ............... 600/476 |
| 5,792,051 | A | | 8/1998 | Chance | |
| 6,045,511 | A | * | 4/2000 | Ott et al. | ..................... 600/504 |
| 6,081,322 | A | | 6/2000 | Barbour | |

(Continued)

FOREIGN PATENT DOCUMENTS

WO        WO 01/20305  A1    9/2000

(Continued)

OTHER PUBLICATIONS

Hull et al., "Noninvasive near-infrared hemoglobin spectroscopy for in vivo monitoring of tumor oxygenation and response to oxygen modifiers." 1997, SPIE, vol. 2979, pp. 355-364.*

(Continued)

*Primary Examiner*—Brian Casler
*Assistant Examiner*—James Kish
(74) *Attorney, Agent, or Firm*—Scully, Scott, Murphy & Presser, P.C.

(57) ABSTRACT

A time series of optical tomography data is obtained for a target tissue site in a human (or animal), using an optical wavelength, such as near infrared, at which hemoglobin is absorptive, to observe properties of the vasculature of the human. The data may be compared to baseline data of a corresponding tissue site, e.g., from a healthy human, or from another, corresponding tissue site of the human. For example, a suspected cancerous breast of a human may be compared to a known healthy breast to detect differences in the vasculature. Measures may be made of flow, oxygen supply/demand imbalance, and evidence of altered regulation of the peripheral effector mechanism. The function of the target tissue site may be analyzed, along with the coordinated interaction between multiple sites of the target system. A provocation may be administered to identify surrogate markers of an underlying state or process.

21 Claims, 5 Drawing Sheets

Tumor Bearing

Normal

U.S. PATENT DOCUMENTS

| | | | |
|---|---|---|---|
| 6,161,031 A * | 12/2000 | Hochman et al. | 600/407 |
| 6,529,846 B2 | 3/2003 | Barbour et al. | |
| 6,577,884 B1 | 6/2003 | Boas | |
| 6,671,540 B1 * | 12/2003 | Hochman | 600/431 |

FOREIGN PATENT DOCUMENTS

| | | |
|---|---|---|
| WO | WO 01/20306 A1 | 9/2000 |
| WO | WO 01/20546 A2 | 9/2000 |

OTHER PUBLICATIONS

Bluestone, A. et al., Three-Dimensional Optical Tomography of Hemodynamics in the Human Head, Optics Express, Sep. 10, 2001, pp. 272-286, vol. 9, No. 6.

Barbour, R. L. et al., Optical Tomographic Imaging of Dynamic Features of Dense-Scattering Media, Journal of the Optical Society of America, Dec. 2001, pp. 3018-3036, vol. 18, No. 12.

Supplementary European Search Report dated Feb. 4, 2009.

\* cited by examiner

SYSTEM AND METHOD FOR QUANTIFYING THE DYNAMIC RESPONSE OF A TARGET SYSTEM

CROSS-REFERENCE TO RELATED APPLICATIONS

This application claims the benefit of U.S. provisional patent application No. 60/370,305, filed Apr. 6, 2002.

STATEMENT REGARDING FEDERALLY SPONSORED RESEARCH OR DEVELOPMENT

This invention was made with government support under grant 1R21 HL67387-01 awarded by the National Heart, Lung and Blood Institute. The government has certain rights in the invention.

BACKGROUND OF THE INVENTION

1. Field of the Invention

This invention relates to applications pertaining to the analysis of noninvasive dynamic near-infrared optical tomography measures of a target system. More particularly, the invention includes the assessment of the target system response and modulation by simultaneously measuring the coordinated interaction between multiple sites of the target system.

2. Description of the Related Art

Many techniques and systems have been developed to image the interior structure of a turbid medium through the measurement of energy that becomes scattered upon being introduced into a medium. Typically, a system for imaging based on scattered energy detection includes a source for directing energy into the target medium and a plurality of detectors for measuring the intensity of the scattered energy exiting the target medium at various locations with respect to the source. Based on the measured intensity of the energy exiting the target medium, it is possible to reconstruct an image representing the cross-sectional scattering and/or absorption properties of the target. Exemplary methods and systems are disclosed in Barbour et al., U.S. Pat. No. 5,137,355, entitled "Method of Imaging a Random Medium," (hereinafter the "Barbour 355 patent"), Barbour, U.S. Pat. No. 6,081,322, entitled "NIR Clinical Opti-Scan System," (hereinafter the "Barbour 322 patent"), and Barbour PCT applications PCT/US00/25156; PCT/US00/25151; PCT/US00/25155 and PCT/US00/25136, all of which are incorporated herein by reference.

Imaging techniques based on the detection of scattered energy are capable of measuring the internal absorption, scattering and other properties of a medium using sources whose penetrating energy is highly scattered by the medium. Accordingly, these techniques permit the use of wavelengths and types of energy not suitable for familiar transmission imaging techniques. Thus they have great potential for detecting properties of media that are not accessible to traditional energy sources used for transmission imaging techniques. For example, one flourishing application of imaging in scattering media is in the field of optical tomography. Optical tomography permits the use of near infrared energy as an imaging source. Near infrared energy is highly scattered by human tissue and is therefore an unsuitable source for straight-line transmission imaging in human tissue (e.g., x-ray imaging). However, these properties make it a superior imaging source for scattering imaging techniques. The ability to use near infrared energy as an imaging source is of particular interest in clinical medicine because it is exceptionally responsive to blood volume and blood oxygenation levels, thus having great potential for detecting cardiovascular disease, tumors and other disease states.

A continuing goal of medical procedures is to obtain objective measures of the state of health and disease. Broadly speaking these measures can be grouped into two classes; those that are performed at a discrete point in time and those that involve essentially continuous measures for a period of time. Examples of the former include many types of blood and urine analyses, tissue biopsy studies, and most forms of medical imaging studies. Prominent examples of the latter include electroencephalographic (EEG) and electrocardiographic (ECG) measures as well as some forms of medical imaging. Common to these is the notion that the information sought after is some assessment of tissue function. When performing such measures it is often desirable, if not essential, to employ noninvasive methods, else the procedure itself can severely bias the measurement. Another feature of these studies is that the measurement employed typically is restricted to providing information about a specific end-organ, usually the heart or brain. More broadly speaking it would be highly desirable, within the capabilities of a single noninvasive measuring technology, to obtain functional information regarding the state of health or disease of specific sites in the body as well as information regarding the coordinated interaction between a target tissue and other body sites. The latter holds relevance, because in many disease states (diabetes, other endocrine and hemotologic disorders, autoinimune, some forms of cancer), the main affliction is considered to originate from a dysregulation in coordinated activities (e.g., autonomic disorders).

Practical realization of these aims poses a number of technical and conceptual challenges. In particular, various known imaging techniques, such as x-ray, magnetic resonance, ultrasound, and positron emission technology (PET) do not lend themselves to assessing the coordinated interaction between a target tissue and other body sites.

SUMMARY OF THE INVENTION

The present invention takes advantage of the fact that the vascular system, which includes arteries, veins and microvessels, is one feature of body function that plays a critical role both at a system wide coordination level and at the local tissue level. The vascular system of a human or animal is interconnected throughout the body, and is known to have many roles. For instance, it is directly responsible for the delivery of essential nutrients and removal of metabolic wastes from tissue. It also plays a critical role in modulating the immune and endocrine response, as well as in controlling body temperature. A notable characteristic of the vasculature that can be well studied using near infrared optical methods is the occurrence of natural beat frequencies. Such oscillations produce rhythmic variations in the luminal diameter of the vessels and hence changes in hemoglobin levels. In addition such techniques can be used to explore changes in the oxygenation level of hemoglobin, such as produced in response to a provocation. Adding to the information value of these measures is the finding that different elements of the vascular tree exhibit distinct natural beat frequencies. For instance, mainly associated with the arterial tree is a cardiac frequency. Similarly, the venous tree exhibits a respiratory beat frequency and the microvessels are modulated in response to a variety of effectors notably neuronal, hormonal and metabolic signals. The examination of these functional properties of the vasculature, as revealed by temporal variations in the hemoglobin signal, provides a unique opportunity to explore integrated local and system wide responses.

Recently, I have described a generic measuring technology whose basic capabilities appear well suited to observing and quantifying such behaviors in tissue structures. The described technology, referred to as dynamic near-infrared optical tomography (DYNOT), is described in the above-identified Barbour and Barbour et al. patents and patent applications. DYNOT provides for a continuous measure of hemoglobin states in deep tissue structures using non-damaging optical sources. Importantly, these assessments can be made in the context of a real-time, 3D imaging modality without the need of exogeneous contrast agents. Image contrast is provided by the natural, or induced, time variations in the hemoglobin signal itself. As described below, I recognize that these capabilities, combined with other techniques, can allow for the development of a general methodology capable of assessing features of the vascular response, including subtle features, that are indicative of local functional states, as well as the system-wide coordination of the vascular response.

In contrast, other imaging techniques such as x-ray, magnetic resonance, ultrasound, and positron emission technology (PET) do not lend themselves to assessing the functionality of the vasculature. Moreover, techniques such as electrical impedance measurements and doppler ultrasound are similarly not satisfactory since, e.g., they are not sensitive to microvessels in the vasculature. The present invention thus recognizes that optical tomography provides the opportunity to assess various aspects of the vasculature that are not accessible by other technologies. Furthermore, it is recognized that the vasculature plays a unique role in the body and can provide important information regarding body function that is not available from other systems, such as the nervous system. It is also recognized that a time series of data that indicates, e.g., differences or comparisons in vascular functioning at different body sites, or at the same site but under different conditions, such as presence or absence of a provocation, can provide valuable information. The invention further recognizes that, given the desirability of studying the functional state of the vasculature, hemoglobin is particularly well-suited for study compared to other components contained within the vasculature, such as albumin, white blood cells or DNA, as it is only hemoglobin that is ordinarily confined to the vascular space and has an appreciable spectral response in the near infrared region where deep penetration occurs. This combination of properties provides a unique opportunity to explore functional states of the vasculature and its functional coupling with the surrounding tissue. It is also the case because of the intrinsic connectivity of the vasculature, use of multisite measures allow for the examination of local and system wide coordinated responses.

In a particular aspect of the invention, a method is provided for assessing tissue function in a subject human or animal. The method includes obtaining a time series of optical tomography data from a first tissue site of the subject human or animal using an optical wavelength at which hemoglobin is absorptive, and comparing this to a corresponding measure from a second tissue site to allow for the assessment of differential responses or coordinated responses. The first tissue site can be any site in the human or animal that is to be analyzed to assess its health. For example, the breast may be analyzed to detect a tumor. The second tissue site can be of the subject human or animal, such as an analogous tissue site of the subject human or animal. In the case of imaging of a breast, the second tissue site may be the contralateral breast, or another quadrant or half of the imaged breast. Or, the second tissue site may be of a completely different are of the body. Or, the second tissue site may be of a baseline human or animal, for example, which is known to be healthy. In the case of humans, the baseline condition may involve comparison to a well trained athlete. In either case, a baseline is thus established by the second tissue site to which the first tissue site is compared.

In a further particular aspect of the invention, a method is provided for assessing tissue function in a subject human or animal. The method includes obtaining first and second time series of optical tomography data from a tissue site of the subject human or animal using an optical wavelength at which hemoglobin is absorptive, provoking the vasculature of the subject human or animal before and/or during the obtaining of the first time series of optical tomography data therefrom, and comparing the first time series of optical tomography data to the second time series of optical tomography data to assess tissue function of the tissue site. The time series of the tissue may be compared at different dates, e.g., days or weeks apart, to assess changes in the tissue, with or without a provocation. A baseline is thus established by one of the time series to which the other time series is compared.

By establishing a baseline, the invention allows the health or disease condition of an individual to be quantified, e.g., by a health index or score, and monitored over the individual's lifetime. The invention also allows the assessment of the time varying behavior of different tissue regions in the body. Simultaneous multi-site measures can be made with respect to a provocation. Temporally and/or spatially superimposed responses may also be analyzed.

BRIEF DESCRIPTION OF THE DRAWINGS

For a better understanding of the invention, together with the various features and advantages thereof, reference should be made to the following detailed description of the preferred embodiments and to the accompanying drawings wherein.

DETAILED DESCRIPTION OF THE INVENTION

Figure 1:
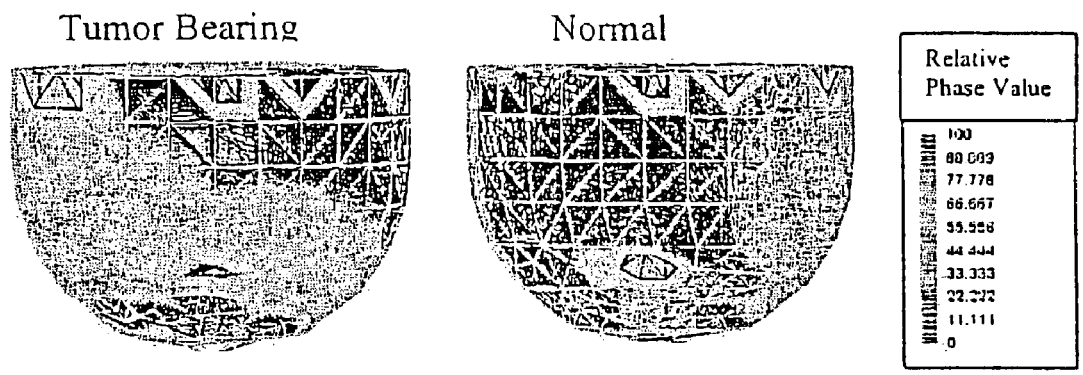
FIG. 1 shows a corresponding phase image of a tumor bearing breast and normal breast.

In a preferred embodiment, the present invention is directed to a general methodology capable of assessing features of the vascular response that are indicative of both local functional states, and a system-wide coordination of the vascular response. The premise for this capability follows from the consideration of five factors.

First is the recognition that because hemoglobin is ordinarily confined to the vascular space, temporal variations in its optical signal can be taken as a reliable indicator of variations in tissue blood volume. To be sure, this concept has been thoroughly substantiated from experience with the methods of photoplethysmography, C. A. Porret, N. Stergiopulos, D. Hayoz, H. R. Brunner, and J. J. Meister, "Simultaneous ipsilateral and contralateral measurements of vasomotion in conduit arteries of human upper limbs," Am. J. Physiology 269, H1852-H1858 (1995), and pulse oximetry, M. R. Neuman, "Pulse oximetry: physical principles, technical realization and present limitations," in Continuous Transcutaneous Monitoring (Advances in Experimental Medicine and Biology, Vol. 220), A. Huch, R. Huch and G. Rooth, Eds. (Plenum Press, New York, 1987), pp. 135-44.

The second consideration is that hemoglobin is not just any blood protein; it is the principal component responsible for oxygen transport to tissue. Thus, variations in its spectral properties can be taken as a reliable indicator of changes in its oxygenation level. Here I do not consider the issue of absolute quantitative measures of hemoglobin oxygenation state in deep tissue structures, but instead focus on the considerable evidence that even simple two-wavelength measures can provide reliable estimates of relative changes in this state, which often is the relevant information sought. Importantly, hemoglobin is also the principal absorbing species in tissue at the illuminating wavelengths I use for imaging. This is especially true as it relates to significant temporal variations in the absorption properties of tissue. Thus I hold that the first two considerations strongly support the contention that time series optical studies mainly identify the hemoglobin signal and in turn, provide a basis for simultaneously defining both local variations in vascular reactivity and hemoglobin oxygenation levels.

The third consideration is the recognition that the principal elements of the vascular tree have distinct natural beat frequencies. Thus, variations in the hemoglobin signal equal to the frequency of ventricular contraction can be reliably taken as originating from the arterial tree. Similarly, it is known that venous return is modulated in synchrony with respiration; hence the veins exhibit a respiratory frequency (~0.3 Hz). It is also known that the diameter of the microvessels, under neural and humoral control, are modulated at still lower frequencies, typically <0.15 Hz. In the context of an imaging scheme, consideration of these frequency bands provides a basis for isolating signals attributable to the major elements of the vascular tree and mapping the spatial distributions of their constitutive and temporal properties.

The fourth consideration is mainly a technical one, but nevertheless holds considerable practical significance. In the context of an imaging modality, analysis of time-varying phenomena carries an added bonus: images having high spatial contrast. The origin of this contrast follows from an appreciation that specific characteristics of time-domain data often can be isolated almost completely. For instance, I have shown by experiment that two nearby objects exhibiting different time-varying behaviors (simulating blood vessels), which were not well resolved in static images, can be resolved from each other with near perfect fidelity, R. L. Barbour, H. L. Graber, Y. Pei, S. Zhong, and C. H. Schmitz, "Optical tomographic imaging of dynamic features of dense scattering media," J. Opt. Soc. Am. A 18, 30 18-3036 (2001). In fact, I have recently extended this finding to show that such imaging capability is mainly independent of the temporal character of the inclusions and their spatial location, even in the limit where both objects are spatially and temporally coincident, H. L. Graber, Y. Pei, and R. L. Barbour, "Imaging of spatiotemporal coincident states by dynamic optical tomography," Proceedings of SPIE Vol. 4250, pp. 153-163 (2001).

The fifth consideration, and unique to dynamic studies, is the expectation that more than one feature may be discerned that serves to distinguish a target (e.g., a tumor) from background or one disease process from another. This state contrasts the situation with static imaging, wherein essentially only one contrast feature is derived (usually, absorption contrast). With dynamic imaging, multiple contrast features can be identified, each producing a high-contrast map. Additionally, consistent with our experience with other time-varying phenomena, these features can often be further discriminated through administration of a defined provocation (e.g., brief arterial occlusion to induce reactive hyperemia). Finally, as with other types of naturally occurring time-varying phenomena (e.g., cardiac rhythms), the influence of a disease process often produces qualitative rather than simply quantitative changes. A differential response of this sort is highly desirable, as it often carries information having high diagnostic sensitivity and specificity.

Among the various features that could be defined from time series imaging of the hemoglobin signal, there are three measures involving tissue-vascular coupling that hold considerable significance in terms of characterizing disease states. These are measures of flow, oxygen supply/demand imbalance, and evidence of altered regulation of the peripheral effector mechanism. Evidence of our ability to image such states in 3D, noninvasively and without the use of contrast agents, is given in the next section. In sum, the ability to simultaneously explore vascular reactivity and local metabolic demand has enormous potential to provide for fundamental strides in attaining new insights into basic physiological processes as well as for developing new approaches to disease detection, prognosis, and guiding therapy.

The method of the present invention is applicable to the realization of practical dynamic imaging of highly scattering media. There are three principal elements to practical dynamic imaging. The first element is the development of a fast, parallel, multi-channel acquisition system that employs geometrically adaptive measuring heads. The second element is to evaluate the acquired tomographic data using the modified perturbation methods. The third element is to collect a time series of data and subject either the time series of data or a time series of reconstructed images from the data to analysis using various linear and nonlinear time-series analysis methods to extract dynamic information and isolated dynamic information. These methods are described in detail in the above-identified Barbour patents and applications.

The methods, systems and experimental results described below focus on optical tomography of human tissue using wavelengths in the near infrared region for the imaging source. However, as disclosed generally herein, it will be appreciated to those skilled in the art that the invention is applicable to the use of essentially any energy source (e.g., electromagnetic, acoustic, and the like) on any scattering medium (e.g., body tissues, oceans, foggy atmospheres, earth strata, industrial materials) so long as diffusive type mechanisms are the principal means for energy transport through the medium.

Moreover, it should be appreciated that FIGS. 1-6, discussed below, are examples of measures of functional information that can be generated from a time series of data that is obtained according to the invention. Various other techniques for analyzing, graphing or otherwise processing data may be used.

1. 3D Imaging of Altered Perfusion States and Disturbances in Tissue Oxygen Supply/Demand in the Cancerous Breast The motivation behind these studies is the well-documented finding that the vascular network that develops in support of solid tumor growth often contains both structural and functional malformations. Not infrequently, the vascular structures present include vessels that are elongated, contain dead-ends, are tortuous and generally leaky. One consequence of this is the blood flow in solid tumors is often sluggish, Vaupel, P. (1995). "Oxygen transport in tumors," in *Oxygen Transport to Tissue XVII (Advances in Experimental Medicine and Biology vol* 388) Ince C; Kesecioglu J; Telci L; Akpir K eds Plenum Press; New York N.Y. 1995;pp. 34 1-51. Another was finding, consistent with a sluggish state of perfusion, evidence that the supply of oxygen to the tumor tissue is only minimally sufficient with regard to demand, thus producing a state wherein the tumor functions on the brink of hypoxemia, Vaupel, P. (1997). "Vascularization, blood flow, oxygenation, tissue PH, and bioenergetic status of human breast cancer, in *Oxygen Transport to Tissue XVIII*, Plenum. To explore these states I have performed time-series imaging studies on the breasts of female volunteers diagnosed with Stage II breast cancer. Subjects were examined while lying prone with one breast hanging pendent through a hole in the patient gantry table beneath which was located an adjustable hemispheric measuring head mounted on a 3-axis translator that served to position the measuring head to allow direct tissue contact. To enhance possible differences between tumor perfusion and that of the surrounding tissue, subjects were asked to perform a series of deep-breathing maneuvers all the while time-series image data were being collected. This protocol was selected as a simple means to modulate venous return. The expected finding is that the presence of a disorganized vascular bed associated with the tumor will cause local delays in tissue perfusion and can be revealed by a spatial map of the phase at the respiratory frequency (normally ~0.3 Hz). An x-ray mammogram of the subject's breast showed a large infiltrating carcinoma measuring 4×7 cm oriented from the lower medial to the upper lateral regions of the breast.

FIG. 1 shows the corresponding phase image recovered from analysis of the Fourier spectrum of the time-series image pixel data. For comparison purposes I also show the corresponding image obtained from the contralateral non-tumor-bearing breast of the same individual following the indicated breathing protocol. Inspection of the phase map for the tumor-bearing breast shows that, with the exception of some surface artifacts, clearly present is a distinct region roughly following the orientation indicated in the x-ray image that has a phase notably distinct from the surrounding tissue. These findings are in contrast to the mainly featureless phase map obtained for the tumor-free breast, suggesting that perfusion is largely coherent. In a second patient I have performed a similar study except that, following the deep-breathing maneuver, the subject was asked to perform a breath-hold for a period lasting approximately one minute. The rationale for this maneuver is that the enhanced metabolic activity associated with a growing tumor, combined with a possible compromised vascular supply, could push the tumor tissue into oxygen debt, causing a decline in the level of oxyhemoglobin together with a rise in the level of deoxyhemoglobin.

Figure 2:
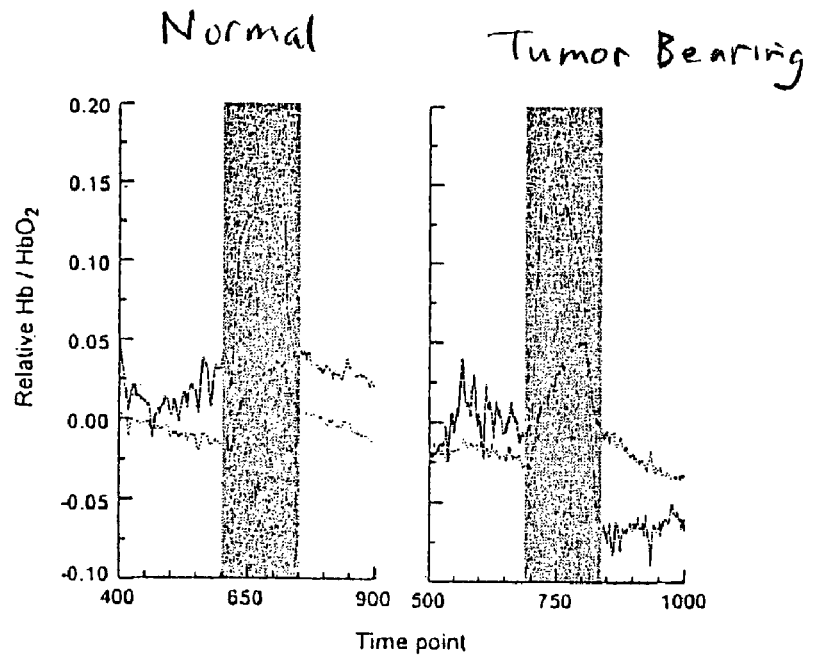
FIG. 2 shows a typical time course of hemoglobin states during a breath hold for a normal breast (left chart) and tumor-bearing breast (right chart)
Figure 3:
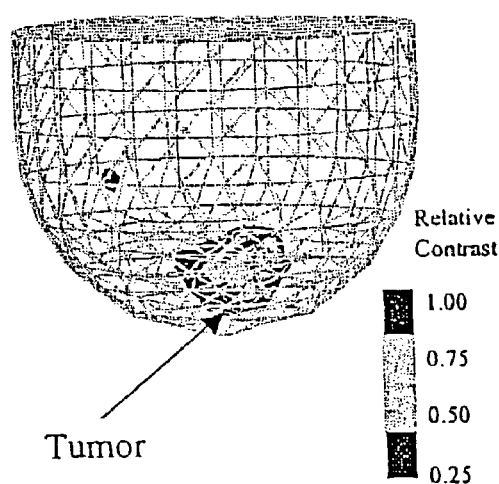
FIG. 3 shows a three dimensional DYNOT image of a tumor.

In FIG. 2, I show a typical time course in the measured normalized levels of oxy- and deoxyhemoglobin obtained before (1), during (2) and after (3) the breath hold for the healthy and tumor-bearing breasts. Comparison between the graphs reveals a qualitatively different trend in hemoglobin states during the breath hold. In both graphs, the oxy- and deoxyhemoglobin (HbO2, Hb, respectively) levels rise initially upon a breath hold, which is the expected response because the associated rise in venous return pressure will cause an increase in tissue blood volume. Following this, I observe that, contrary to the trend seen in the healthy breast, the HbO2 level in the tumor-bearing breast becomes unstable and then declines, accompanied by a steeper rise in the level of deoxyhemoglobin. These findings are entirely consistent with the well-recognized general finding that solid tumors function on the brink of hypoxemia. In FIG. 3 I show an example of how this information, extracted from a time-series of tomographic measurements, can serve to image the tumor with high contrast.

Shown in the FIG. 3 is an isocontour plot of the product of the slopes of the lines obtained by performing linear regressions on the data points within the indicated time interval (gray zone) for the HbO2 and Hb levels seen during the breath-hold, from the pixel data corresponding to the computed 3D image time series. For presentation clarity, I show only those contour levels that comprise the highest 90% of the computed values (i.e., background contrast is <10% of the maximum value shown). Comparison of this result to a sonogram image of the same breast indicates excellent agreement in terms of tumor size and location. The equivalent result obtained from the normal breast (not shown) showed an image that was essentially featureless for the contrast ranges shown. Note that the size of the tumor in this subject is considerably smaller than in the first subject, measuring approximately 1.5-2.0 cm in diameter.

2. Imaging of Functional Disturbance in Peripheral Effector Mechanism of Tumor Vasculature: A Time-Frequency Study.

It is well established that the resting vasomotor tone can be influenced by acute changes in the local tissue environment, L.-F. Zhang, "Vascular adaptation to microgravity: what have we learned?,".1. *Applied Physiology* 91, 2415-2430 (2001) and that chronic disturbances can lead to observable changes in gene expression involving at least the vascular endothelium, Y. Yokota, Y. Imaizumi, M. Asano, T. Matsuda, and M. Watanabe, "Endothelium-derived relaxing factor released by 5-HT: distinctive from nitric oxide in basilar arteries of normotensive and hypertensive rats," *Br. J Pharmacology* 113, 324-330 (1994) and possibly other components of the peripheral effector mechanism. One factor well studied is the influence of hypoxia, U. Zwiener, D. Hoyer, R. Bauer, B. Luthke, B. Walter, K. Schmidt, S. Hallmeyer, B. Kratzsch, and M. Eiselt, "Deterministic-chaotic and periodic properties of heart rate and arterial pressure fluctuations and their mediation in piglets," *Cardiovascular Research* 31, 455-465 (1996). This state is commonly encountered in solid tumors, and thus the finding of altered gene expression of the vascular endothelium of these tissues may not be coincidental, B. St. Croix, C. Rago, V. Velculescu, G. Traverso, K. E. Romans, E. Montgomery, A. Lal, G. J. Riggins, C. Lengauer, B. Vogelstein, and K. W. Kinzler, "Genes expressed in human tumor endothelium," *Science* 289, 1197-1202 (2000). This suggests that one consequence of altered gene expression might be a concomitant change in the response characteristics of the effector complex and its modulation by local and systemic modulators (hormonal or neural signals). To test this hypothesis, I have employed time-frequency analysis techniques to identify possible alterations in the modulation of prominent vascular frequencies in normal and tumor-bearing breasts. This was accomplished by performing baseline measures of the breast, lasting approximately 20 minutes, on subjects at rest and computing the Fourier spectra of temporal variations in the amplitudes of the nominal carrier frequencies. The latter were determined by a simple Fourier transform computation of measured baseline time-series detector readings, and are here referred to as the carrier spectrum. As physiological data are generally non-stationary, I have also computed a (continuous Morlet) wavelet transform to determine the temporal dependence of the amplitudes and phases of the carrier spectrum. The occurrence of distinct modulation frequencies within these time-varying data can be obtained by computing their frequency spectra.

Figure 4:
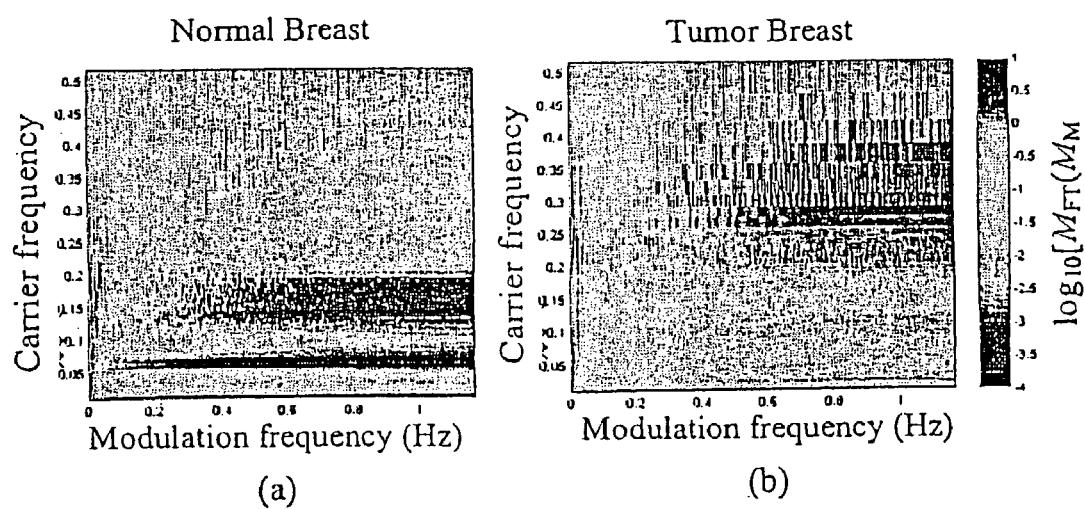
FIG. 4 illustrates modulation amplitude surfaces for a normal breast and tumor-bearing breast.
Figure 5:
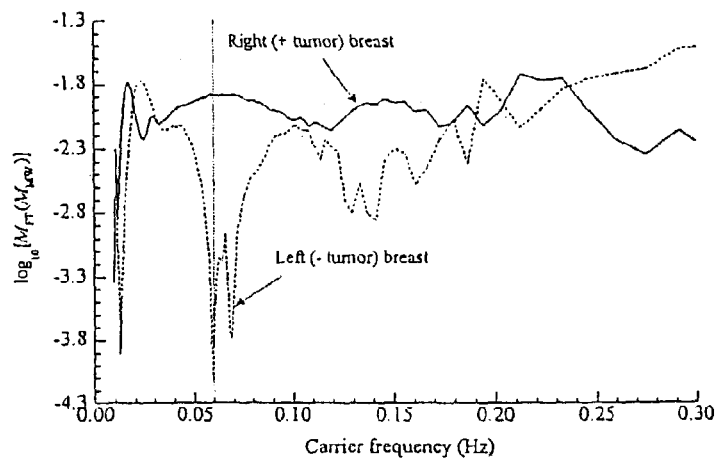
FIG. 5 shows the modulation amplitude as a function of carrier frequency.
Figure 6:
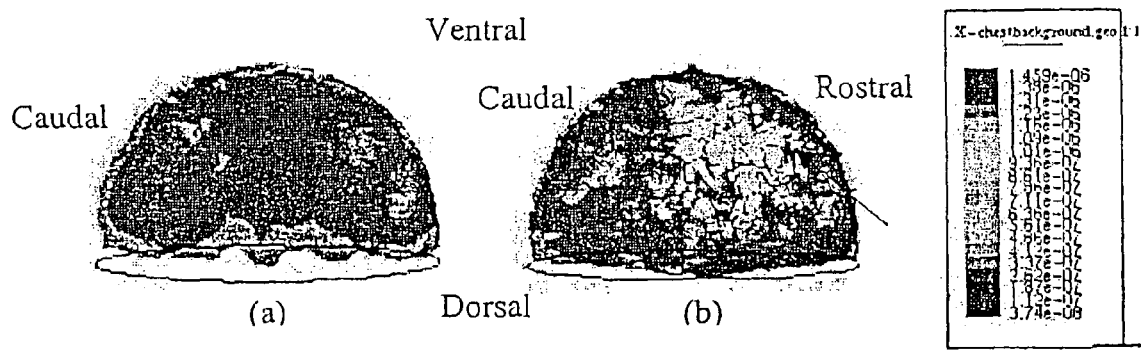
FIG. 6 shows a computed three dimensional volume rendered image of the modulation amplitude for a normal breast and tumor-bearing breast.

Results shown in FIG. 4 illustrate the strength of modulation as a function of the carrier frequency, for a selected set of detector values in a tumor-bearing and contralateral non-tumor-bearing breast for a subject having a Stage II tumor. A brief comparison reveals that there are distinct differences in the modulation amplitude. A clear example of this can be seen in FIG. 5, which shows the modulation amplitude as a function of carrier frequency at a specified modulation frequency (0.25 Hz). Inspection of this figure shows that there are distinct frequencies where the amplitude of modulation in the normal breast is notably lower (~0.01, 0.06 and 0.07 Hz) than in the tumor-bearing breast. I note that a qualitatively similar response has been observed in at least one other subject thus far examined (results not shown). In FIG. 6 a computed 3D volume-rendered image of the modulation amplitude for the carrier frequency indicated in FIG. 5 is shown. Inspection reveals that a region having notably higher amplitude at this frequency is present in the tumor-bearing breast compared to the contralateral breast (lateral aspect half-way between chest wall and nipple), and that this location coincides reasonably well with the ultrasound image of the tumor (tumor measuring 1×1×2 cm, located approximately 2 cm subsurface at 11 o'clock and 7 cm laterally from the nipple). I take this finding to suggest that results from DYNOT studies has the potential to serve as a surrogate marker for altered gene expression as reflected by changes in the modulating features of the basal vascular response. Should this finding be specific, it would directly provide a means to non-invasively, and without need of exogeneous contrast agents, identify subjects having characteristic gene profiles whose particulars may be amenable to selected molecular targeting.

3. System Design.

Figure 7:
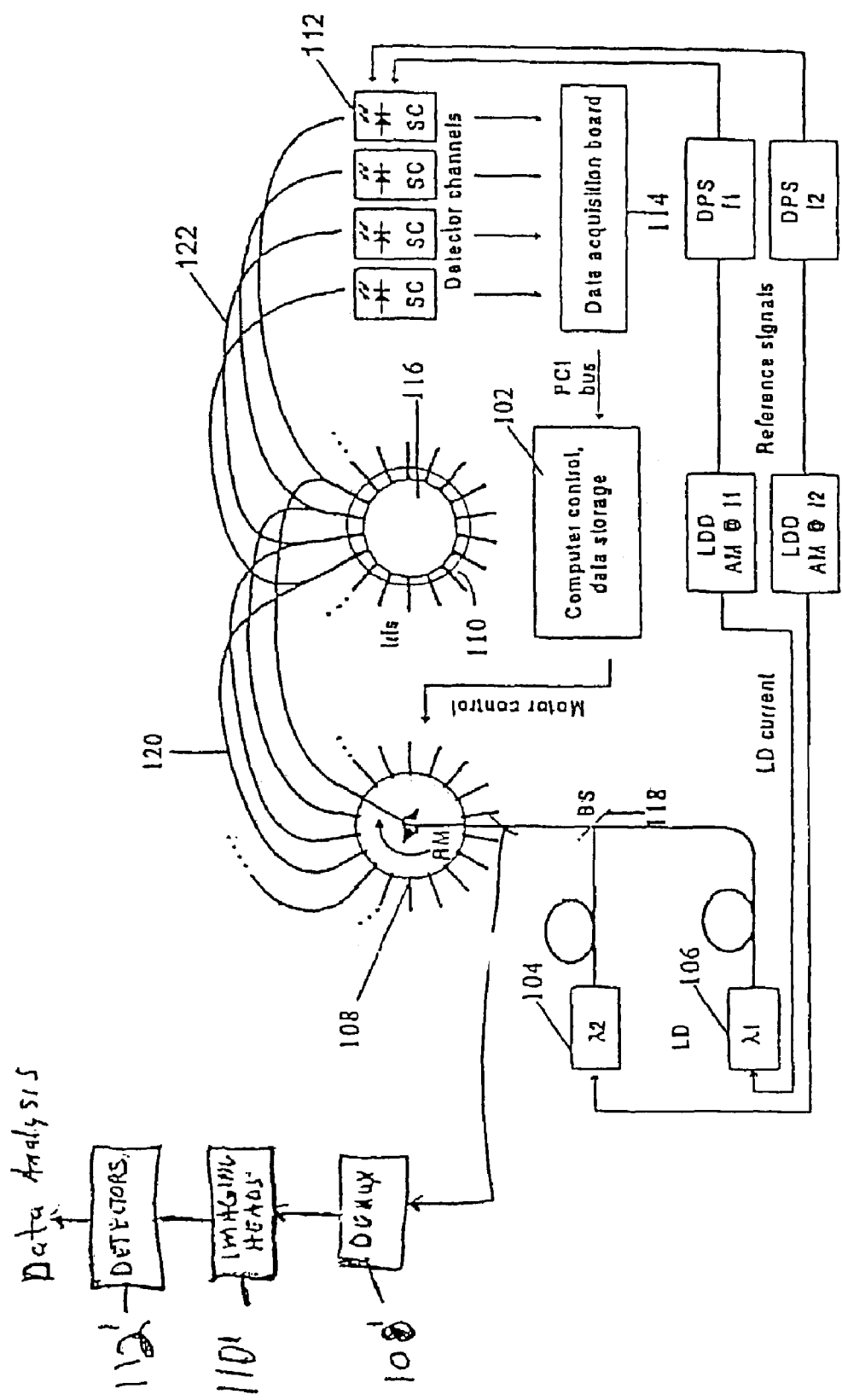
FIG. 7 is a schematic illustration of an exemplary imaging system of the present invention.

The following is a description of an exemplary system hardware and software design that comprise the DYNOT system. Numerous imaging systems such as those disclosed in the Barbour '355 patent, Barbour '322 patent and the Barbour applications identified above have been developed for use in imaging of a scattering medium. A schematic illustration of an exemplary system is shown in FIG. 7. This system includes a computer 102, sources 104, 106, a source demultiplexer 108, an imaging head 110, detectors 112 and a data acquisition board 114. In a system for imaging in multiple regions of the body, one or more sets of a demultiplexer 108', imaging head 110' and detectors 112' are also provided.

A target 116 placed in the imaging head 110 is exposed to optical energy from sources 104, 106. The optical energy originating from sources 104, 106, is combined by beam splitter 118 and is delivered to source demultiplexer 108. The source demultiplexer 108 is controlled by computer 102 to direct the optical energy to source fibers 120 sequentially.

Each source fiber 120 carries the optical energy from the demultiplexer 108 to the imaging head 110, where the optical energy is directed into the target 116. The imaging head 110 contains a plurality of source fibers 120 and detector fibers 122 for transmitting and receiving light energy, respectively. Each source fiber 120 forms a source-detector pair with each detector fiber 122 in the imaging head 110 to create a plurality of source detector pairs. The optical energy entering the target 116 at one location is scattered and may emerge at any location around the target 116. The emerging optical energy is collected by detector fibers 122 mounted in the imaging head 110.

The detector fibers 122 carry the emerging energy to detectors 112, such as photodiodes or a CCD array, that measure the intensity of the optical energy and deliver a corresponding signal to a data acquisition board 114. The data acquisition board 114, in turn, delivers the data to computer 102. The computer is configured and programmed to carry out the techniques described herein.

This imaging process is repeated so as to deliver optical energy to each of the source fibers sequentially, a measurement being obtained for detected emerging energy at each detector for each emitting source fiber. This process may continue over a period of time with the computer 102 storing the data for reconstruction of one or more images. Additionally, the system may include two or more imaging heads for comparing one target to another. The computer 102 reconstructs an image representative of the internal optical properties of the target by solving a perturbation equation. It will be appreciated by those skilled in the art that more than one computer can be used to increase data handling and image processing speeds.

Figure 8:
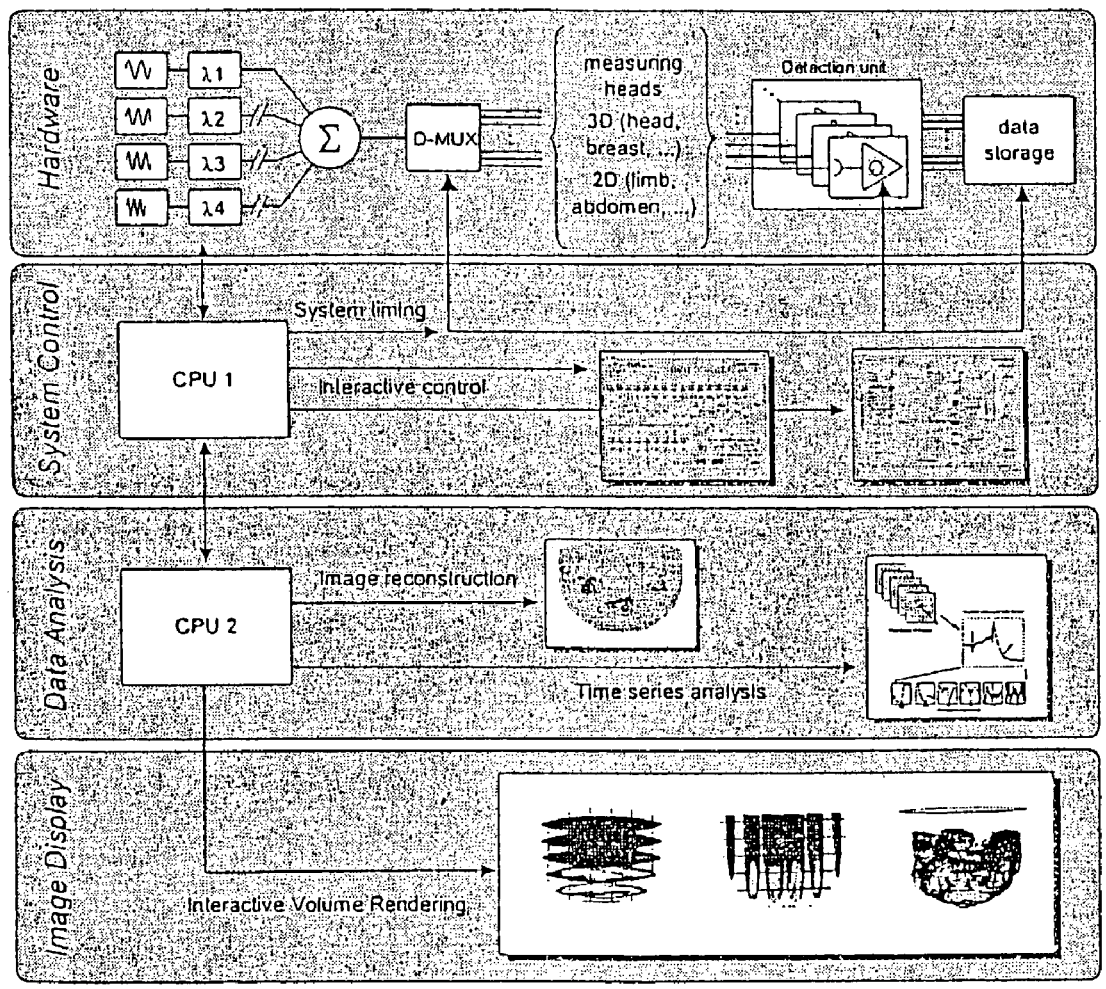
FIG. 8 illustrates the functional layout of an imaging system according to the present invention.

The system employs an architecture that comprises seven levels of hardware/software functionality (see FIG. 8). The hardware level features use of frequency-encoded multi-wavelength DC illumination, a time-multiplexed source, and parallel multi-channel detection, together with on-the-fly fast gain switching (dynamic range 180 dB). Fully configured, the basic unit can provide four wavelengths of simultaneous illumination at each illuminating site, and collect data from 32 channels at a source switching rate of 90 Hz. This provides a data acquisition rate of between 2.2 and 8.8 kHz. System operation is achieved through two levels of software control. The first level is transparent to the operator and is responsible for system timing and data storage. The second level serves as the user interface and includes functions for optical alignment, instrument calibration, offset correction and automated/manual gain adjustment.

Other functionalities include specification of illuminating wavelengths, phase adjustment, selection of the source illumination scheme (single site or tomographic illumination), number of image frames, and data path. This is accomplished using a virtual instrument panel generated within a LabVIEW environment. The collected data are made available to four additional levels of data processing to provide for data viewing and analysis in real time. Three of these are handled by a second CPU networked to the system controller. The first level, provided by the system controller and under the Lab VIEW environment as well, serves a viewing screen that displays the measured intensity data for all (selected) source detector pairs in real time. This is presented in scrolling format that is color-coded to indicate different intensity levels. Various viewing formats are available. These include the raw intensity data, normalized values, and computed values of hemoglobin states. The viewing screen provides additional functionalities that allow interactive adjustment of viewing parameters for operator convenience. The second CPU, operating in a Unix environment, provides additional levels of data processing associated with image reconstruction, image display and image analysis. A variety of coupled forward-inverse reconstruction algorithms is available. These allow for image recovery using first-order or recursive finite element based schemes, for 2D or 3D problems. All are derived from the diffusion equation for DC illumination. Computed parameters include absorption only, scattering (diffusion) only, or both. Real-time image recovery (2D or 3D) may be accomplished using techniques, such as SVD-based back substitution, which enhance computational speed and stability, as described in Barbour et al. U.S. provisional patent application No. 60/370,306, filed Apr. 6, 2002, priority of which is claimed in co-pending U.S. patent application Ser. No. 10/408,511, filed Apr. 6, 2003, and entitled "Modification Of The Normalized Difference Equation For Real-Time Optical Tomography," incorporated herein by reference. The image display provides for a variety of viewing formats and has interactive capabilities. The computed image series is also available for offline interrogation using a spectrum of analysis routines of the design embedded within an interactive MATLAB environment. These allow for the computation and display of linear and nonlinear properties associated with the time-varying pixel data.

A method of the present invention comprises:

1. Identify target tissue(s) and complementary independent measures to be made at one or more separate sites or regions of the target object.

2. Perform baseline DYNOT measures and/or measures involving a defined provocation. These can involve one or more target tissues that are evaluated sequentially or simultaneously before during and/or after introducing a physiologic and/or metabolic challenge. These measures may be supplemented with one or more independent physiologic and/ or metabolic measures temporally coincident, or nearly so, with the DYNOT exam. The DYNOT method comprises the following steps:

(1) selecting a reference medium having known boundary conditions and optical properties which are substantially similar to those of the intended target;
   (2) determining a weight matrix and an intensity of emerging energy exiting the reference medium at each of a plurality of source points for each of a plurality of detectors located around the reference medium boundary, the determination being made by either actual measurements or solution of the radiation transport equation;
   (3) measuring actual emerging energy intensities for corresponding source and detector points on a target medium; and
   (4) solving the perturbation equation for the optical properties of the target based on the measured intensities of energy emerging from the target.

3. Extract relevant parameters from DYNOT measures and associated independent measures to determine multi-parameter response. Time series data can include individual or composite measures of optical detector responses, computed hemoglobin states and/or corresponding results from derived optical image time series. Extracted parameters can include measures derived from time-frequency analysis of the primary or modulated signals.

4. Apply model-based or empirical data reduction schemes (e.g., general linear model) to derive statistically valid markers.

5. Derived markers may serve as the primary or surrogate indicator of considered state.

EXAMPLES OF CHALLENGE TESTS

I. Physiological Maneuvers.
   1. Assessment of Autonomic Function
      a) Quantitative Valsalva maneuver
      b) Table Tilt
      c) Cold Shock -continued 2. Autoregulatory Vascular Response.
      a) Reactive Hyperemia
      b) $CO_2$ Challenge Test.
II. Metabolic/Pharmacological Maneuvers.
   a) Glucose (other metabolic) Tolerance Test
   b) Insulin (other hormone) Challenge Test
   c) Other Pharmacological Agents (acute or chronic assessments)
III. Dietary/Physical Conditioning Assessment.
   a) Response to dietary supplements/monitoring.
   b) Guide to physical conditioning.

The listed maneuvers are intended to impose defined provocations on the vasculature that in many cases will produce a response indicative of the functional state of the vascular apparatus and its interaction with surrounding tissue. Depending on the underlying disease process or biochemical/ pharmaceutical agent being studied, characterization of measured responses will allow for the identification of signatures that serve as surrogate markers of the underlying state or process.

Application Areas Include:

1. Breast and other tissue cancer detection, prognosis and treatment monitoring.

2. Assessment of allograph rejection (e.g., renal transplant).

3. Monitoring of immune/inflammatory/wound-repair response.

4. Surrogate marker for gene expression of vascular endothelium/smooth muscle apparatus.

5. Early marker for diabetes-induced microvascular pathology (protein glycoslation, peripheral neuropathy, vascular occlusion).

6. Examination of neurovascular response to cognitive/ sensory/motor activation.

7. Assessment of integrated cardiovascular response to autonomic stimuli/dysfunction.

8. Acute care monitoring (e.g., assessment of peripheral vascular resistance).

9. Assessment of tissue-vascular response to pharmacoactive agents dietary supplements, and/or physical conditioning.

10. In additional to imaging hemoglobin, the invention can be used to image another protein or an injected dye, for instance. Essentially, any substance confined to the vascular space can be imaged.

11. Blood volume changes can be measured, e.g., to detect compartment syndrome.

12. Measuring the effects of drugs, e.g., whether they are local or global in the body.

The invention has been described herein with reference to particular exemplary embodiments. Certain alterations and modifications may be apparent to those skilled in the art, without departing from the scope of the invention. The exemplary embodiments are meant to be illustrative, not limiting of the scope of the invention, which is defined by the appended claims.

What is claimed:

1. A method for assessing tissue function in a subject human or animal, comprising:

obtaining simultaneously a time series of optical tomography data from a first tissue site and a second tissue site of the subject human or animal, the first tissue site and the second tissue site being located at different areas of the subject human or animal, wherein the time series of optical tomography data from the first tissue site and the second tissue site identify temporal variations in at least one hemoglobin signal by illuminating a radiation at a wavelength at which hemoglobin is a principal absorbing species in the first and second tissues;

comparing the time series of optical tomography data from the first tissue site to the time series of corresponding optical tomography data from the second tissue site;

deriving a first time series of optical tomography images from the time series of optical tomography data from the first tissue site;

deriving a second time series of optical tomography images from the time series of optical tomography data from the second tissue site;

assessing differential responses or coordinated responses from the first tissue site and the second tissue site by determining a functional property of a vasculature through examination of said temporal variations in said at least one hemoglobin signal; and generating a real-time 3D image based on said determining of said functional property of said vasculature, wherein image contrast is provided by employing said temporal variations in said at least one hemoglobin signal.

2. The method of claim 1, wherein the comparing step further comprises comparing phase differences in the optical tomography data or differences in hemoglobin states between the first and second tissue sites.

3. The method of claim 1, wherein the comparing step further comprises comparing a modulation amplitude of the optical tomography data as a function of carrier frequency for the first and second tissue sites.

4. The method of claim 1, wherein the comparing step further comprises comparing variations in the optical tomography data for the first and second tissue sites at a frequency band associated with a vascular beat frequency of the subject human or animal.

5. The method of claim 1, wherein the second tissue site is from a baseline human or animal that is known to be healthy.

6. The method of claim 1, further comprising: provoking said vasculature before or during the obtaining of the time series of optical tomography data therefrom.

7. The method of claim 6, wherein the step of provoking further includes provoking using physiological maneuver, metabolic maneuver, metabolic maneuver, dietary conditioning, or physical conditioning, or combinations thereof.

8. The method of claim 1, wherein the first tissue site and the second tissue site are contralateral areas of said subject human or animal.

9. The method of claim 1, wherein said at least one hemoglobin signal includes a hemoglobin level or an oxygen level of hemoglobin.

10. The method of claim 1, further comprising provoking vasculature of the subject human or animal during said obtaining step to assess differential responses or coordinated responses from the first tissue site and the second tissue site.

11. The method of claim 1, wherein the deriving steps include reconstructing the first time series of optical tomography images and the second time series of optical tomography images by solving a perturbation equation using respectively the time series of optical tomography data from a first tissue site and the time series of optical tomography data from the second tissue site.

12. A method for assessing tissue function in a subject human or animal, comprising:

obtaining simultaneously first and second time series of optical tomography data from first and second tissue sites of the subject human or animal, the first tissue site and the second tissue site being located at different areas, wherein the first and second time series of optical tomography data from the first and second tissue sites identify temporal variations in at least one hemoglobin signal by illuminating a radiation at a wavelength at which hemoglobin is a principal absorbing species in the first and second tissues;

comparing the first time series of optical tomography data to the second time series of optical tomography data to assess tissue function of the tissue site;

deriving a first time series of optical tomography images from the first time series of optical tomography data; and deriving a second time series of optical tomography images from the second time series of optical tomography data;

assessing differential responses or coordinated responses from the first tissue site and the second tissue site by determining a functional property of a vasculature through examination of said temporal variations in said at least one hemoglobin signal; and generating a real-time 3D image based on said determining of said functional property of said vasculature, wherein image contrast is provided by employing said temporal variations in said at least one hemoglobin signal.

13. The method of claim 12, wherein the comparing step further comprises comparing phase differences of the optical tomography data in the first and second time series.

14. The method of claim 12, wherein the comparing step further comprises comparing hemoglobin states for the first and second time series.

15. The method of claim 12, wherein the comparing step further comprises comparing a modulation amplitude of the optical tomography data as a function of carrier frequency for the first and second time series.

16. The method of claim 12, wherein the comparing step further comprises comparing variations in the optical tomography data for the first and second time series at a frequency band associated with a vascular beat frequency of the subject human or animal.

17. The method of claim 12, further comprising: provoking said vasculature before or during the obtaining of the first time series of optical tomography data therefrom.

18. The method of claim 12, further comprising provoking vasculature of the subject human or animal during said obtaining step using physiological maneuver, metabolic maneuver, pharmacological maneuver, dietary conditioning, or physical conditioning or combinations thereof, to assess differential responses or coordinated responses from the first tissue site and the second tissue site.

19. The method of claim 12, wherein the deriving steps include reconstructing the first time series of optical tomography images and the second time series of optical tomography images by solving a perturbation equation using respectively the time series of optical tomography data from a first tissue site and the time series of optical tomography data from the second tissue site.

20. A method for assessing tissue function in a subject human or animal, comprising:

obtaining simultaneously without using contrast agent a time series of optical tomography data from a first tissue site and a second tissue site of the subject human or animal, the first tissue site and the second tissue site being located at different areas of the subject human or animal, wherein the first and second time series of optical tomography data from the first and second tissue sites identify temporal variations in at least one hemoglobin signal by illuminating a radiation at a wavelength at which hemoglobin is a principal absorbing species in the first and second tissues;

provoking a vasculature of the subject human or animal during said obtaining step using physiological maneuver, metabolic maneuver, pharmacological maneuver, dietary conditioning, or physical conditioning or combinations thereof;

comparing the time series of optical tomography data from the first tissue site to a time series of corresponding optical tomography data from a second tissue site;

deriving a first time series of optical tomography images from the time series of optical tomography data from the first tissue site;

deriving a second time series of optical tomography images from the time series of optical tomography data from the second tissue site;

assessing differential responses or coordinated responses from the first tissue site and the second tissue site by determining a functional property of said vasculature through examination of said temporal variations in said at least one hemoglobin signal; and generating a real-time 3D image based on said determining of said functional property of said vasculature, wherein image contrast is provided by employing said temporal variations in said at least one hemoglobin signal.

21. The method of claim 20, wherein the deriving steps include reconstructing the first time series of optical tomography images and the second time series of optical tomography images by solving a perturbation equation using respectively the time series of optical tomography data from a first tissue site and the time series of optical tomography data from the second tissue site.

* * * * *

UNITED STATES PATENT AND TRADEMARK OFFICE
CERTIFICATE OF CORRECTION

PATENT NO.       : 7,778,693 B2
APPLICATION NO.  : 10/408510
DATED            : August 17, 2010
INVENTOR(S)      : Randall L. Barbour et al.

It is certified that error appears in the above-identified patent and that said Letters Patent is hereby corrected as shown below:

Title Page, Item (73) should read
--(73) Assignee: National Institutes of Health (NIH), U.S. Dept. of Health and Human Services, (DHHS), U.S. Government, Bethesda, MD (US)--.

Signed and Sealed this

Fifth Day of October, 2010

David J. Kappos
*Director of the United States Patent and Trademark Office*